US006841126B2

(12) United States Patent
Oonuma et al.

(10) Patent No.: US 6,841,126 B2
(45) Date of Patent: Jan. 11, 2005

(54) AUTOMATIC ANALYZER

(75) Inventors: Mitsuru Oonuma, Tokyo (JP); Atsushi Ninomiya, Ome (JP); Tadashi Ohishi, Ibaraki (JP)

(73) Assignee: Hitachi, Ltd., Tokyo (JP)

( * ) Notice: Subject to any disclaimer, the term of this patent is extended or adjusted under 35 U.S.C. 154(b) by 375 days.

(21) Appl. No.: 09/901,892

(22) Filed: Jul. 11, 2001

(65) Prior Publication Data

US 2002/0025275 A1 Feb. 28, 2002

(30) Foreign Application Priority Data

Aug. 28, 2000  (JP) ........................................ 2000-257578

(51) Int. Cl.⁷ ............................................. G01N 21/01
(52) U.S. Cl. ........................... 422/64; 422/104; 436/47; 436/48
(58) Field of Search ...................... 435/287.3; 422/64, 422/104; 436/47, 48

(56) References Cited

U.S. PATENT DOCUMENTS

| | | | | |
|---|---|---|---|---|
| 4,483,823 A | * | 11/1984 | Umetsu et al. | 422/63 |
| 4,595,562 A | * | 6/1986 | Liston et al. | 422/65 |
| 6,440,369 B1 | * | 8/2002 | Oonuma et al. | 422/64 |

FOREIGN PATENT DOCUMENTS

WO  WO97/09621  * 3/1997

OTHER PUBLICATIONS

Patent Abstracts of Japan, Publication No. 06–088828 (Application No. 04–239519), published Mar. 29, 1994.*
Patent Abstracts of Japan, Publication No. 59–022905 (Application No. 52–69908).*

* cited by examiner

*Primary Examiner*—Jan M. Ludlow
(74) *Attorney, Agent, or Firm*—Antonelli, Terry, Stout & Kraus, LLP

(57) ABSTRACT

It is an object of the present invention to provide a small-sized automatic analyzer that is convenient in use, wherein an insertion of an urgent sample can be easily carried out, its safety in operation and operability can be improved and its erroneous operation can be prevented. In order to accomplish the object of the present invention, a top panel of a body is provided with a sample disk storing a plurality of sample cups, a reagent disk storing a plurality of reagent bottles, and a reaction disk storing a plurality of reaction cuvettes for reacting sample liquid in sample cups with the reagent in reagent bottles and there is arranged an indicator illuminated when the sample disk is stopped, and there is provided a cover for covering a part of the top panel of the body, and when the cover is closed, a part of the sample disk is exposed out of the cover. The sample disk is provided with sample disk covers constituted in two-divided segments, and one of the covers is arranged at a position where it is removably exposed outside the cover when the cover is closed.

11 Claims, 6 Drawing Sheets

FIG. 6
SELECTED 5th PERCENTILE FEMALE 1471mm, 95th PERCENTILE MALE 1895mm STANDING DIMENSIONS

AUTOMATIC ANALYZER

BACKGROUND OF THE INVENTION

This invention relates to an automatic analyzer convenient in use in which both an urgent sample insertion keeping its safety and operability of an operator can be improved, and any erroneous operation can be prevented.

As the prior art in regard to an automatic analyzer, it is well known to apply the technology described in the gazette of Japanese Unexamined Patent Publication No. Sho 59-22905, for example. Although the technology before this prior art described above needed one feeder mechanism for each of a plurality of reagents, the prior art simplified the mechanism in such a way that only two feeder mechanisms were satisfactorily provided even if a plurality of reagents were applied. In addition, as a further prior art, it is well known to apply a technology described in the gazette of Japanese Unexamined Patent Publication No. Hei 6-88828. This prior art is made such that the reaction cuvettes is constructed as a double-walled one or a three-layer walled one, each of the rows of reaction cuvettes is made as an independent one, the reaction cuvettes can be washed and continuously processed for every steps of each of the reactions in order to increase a processing capability to enable all the reactions to be carried out in parallel within the same time and to prevent any contamination from being generated between the reagents.

All the aforesaid prior arts have some problems that a sufficient study is not provided for a small-sized formation of the device, a wide location is needed, and in addition an arrangement about either an operating section for controlling the device or a display device is not devised, and it is not satisfactory in view of an easiness or safety in operation for an operator or prevention in erroneous operation.

SUMMARY OF THE INVENTION

This invention relates to an automatic analyzer, and more particularly an automatic analyzer in which a row of reaction cuvettes is turned across an optical path of photometer to perform a biochemical inspection or immune inspection.

It is an object of the present invention to provide a small-sized automatic analyzer convenient in use in which the aforesaid problems of the prior art can be overcome, both an urgent sample insertion keeping its safety and operability of an operator can be improved, and any erroneous operation can be prevented.

In accordance with the present invention, the aforesaid object is accomplished by the automatic analyzer for performing a biochemical inspection or immune inspection, wherein a sample disk storing a plurality of sample cups, a reagent disk storing a plurality of reagent bottles and a reaction disk storing a plurality of reaction cuvettes for reacting sample liquid in the sample cup with reagent are arranged at a top panel of a body and an indicator illuminated at the time of stopping of the sample disk is arranged.

In addition, the aforesaid object is accomplished by an arrangement in which there is provided a cover covering a part of a top panel surface of the body and a part of the sample disk is exposed out of the cover when the cover is closed, and additionally the indicator is arranged near the sample disk at a position where it is exposed outside the cover when the cover is closed.

Further, the aforesaid object is accomplished by an arrangement in which the sample disk is provided with a sample disk cover constituted in two-divided segments, the two-divided segment cover for the disk cover of the feeder is positioned inside the cover when the cover is closed and the other cover is arranged at a position where it is exposed outside the cover when the disk cover is closed, and the disk cover at the feeder is provided with a protection plate.

DESCRIPTION OF THE PREFERRED EMBODIMENT

Referring now to the drawings, one preferred embodiment of an automatic analyzer of the present invention will be described in detail as follows.

Figure 1:
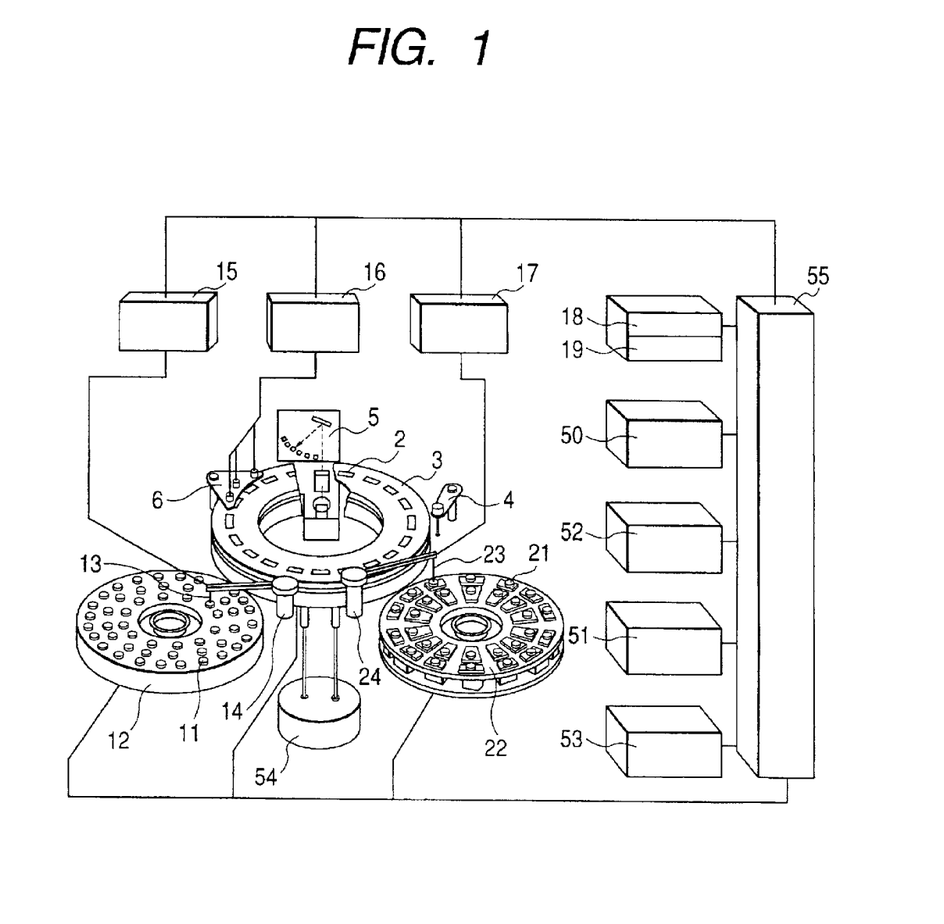
FIG. 1 is a principle view for illustrating a functional configuration of an automatic analyzer to which the present invention is applied.

FIG. 1 is a principle view for illustrating a functional configuration of an automatic analyzer to which the present invention is applied. Before describing the preferred embodiment of the present invention, a principle of a major segment of the automatic analyzer to which the present invention is applied will be described at first. In FIG. 1, reference numeral 2 denotes a reaction cuvette; 3 is a reaction disk; 4 is a mixing mechanism; 5 is a photometer; 6 is a rinse mechanism; 11 is a sample cup; 12 is a sample disk; 13 is a nozzle; 14 is a serum sampling mechanism; 15 is a serum pipettor; 16 is a washing pump; 17 is a reagent pipettor; 18 is a LG amplifier unit; 19 is an A/D converter unit; 21 is a reagent bottle; 22 is a reagent disk; 23 is a reagent nozzle; 24 is a reagent pipetting mechanism; 50 is a computer; 51 is a outputting printer; 52 is an LCD; 53 is a floppy disk mechanism; 54 is an incubation bath; and 55 is an interface, respectively.

The automatic analyzer shown in FIG. 1 has, as its major composing elements, the rotary type reaction disk 3 holding a plurality of transparent plastic reaction cuvettes 2; the rotary type reagent disk 22 holding a plurality of reagent bottles 21; the rotary type sample disk 12 holding the sample cups 11 for storing each of a plurality of measured samples and a plurality of standard samples; and the photometer 5 for measuring an absorbance of the reaction cuvettes 2 at a predetermined wavelength in response to inputted information.

In addition, the automatic analyzer shown is comprised of the serum sampling mechanism 14 (hereinafter called as a sample feeder) for sucking each of sample liquid of predetermined amount into the nozzle 13 in response to inputted sample information from the sample cup 11 at the specified position of the sample disk 12 and discharging the sample to the reaction cuvettes 2 at the specified position of the reaction disk 3; and the serum pipettor 15. Further, the automatic analyzer shown is comprised of the reagent pipetting mechanism 24 (hereinafter called as a reagent feeder) and the reagent pipettor 17. These mechanisms are rotated in response to inputted sample information, suck the predetermined amount of reagent based on the inputted information from the reagent container 21 which is a reagent bottle placed at a reagent sucking position on the reagent disk 22 having its stopping position controlled into the reagent nozzle 23 held at a movable arm and add the reagent to the sample liquid already stored in the reaction cuvettes 2 placed at the reagent discharging position on the reaction disk 3. The aforesaid two kinds of liquid stored in the reaction cuvettes 2 are mixed by the mixing mechanism 4 for the reaction liquid and the mixing position is coincided with the reagent discharging position on the reaction disk 3.

In addition to the aforesaid mechanisms, the automatic analyzer shown is comprised of the photometer 5 for measuring an absorbance of each of the reaction cuvettes 2 across an optical axis with a predetermined wavelength based on inputted information when the reaction disk 3 is rotated; the rinse mechanism 6 for rinsing the reaction cuvettes 2 upon completion of measurement; the washing pump 16; the LG amplifier 18; the A/D converter 19; the computer 50 for controlling operation of each of the mechanisms and for processing data; the outputting printer 51; the LCD 52 with input/output and displaying touch panels; the floppy disk mechanism 53 for a program, a measuring condition and a data memory; the incubation bath 54 for holding each of the reaction cuvettes 2 on the reaction disk 3 at a specified temperature; and the interface 55 for connecting the computer with each of the mechanisms or the like.

Figure 2:
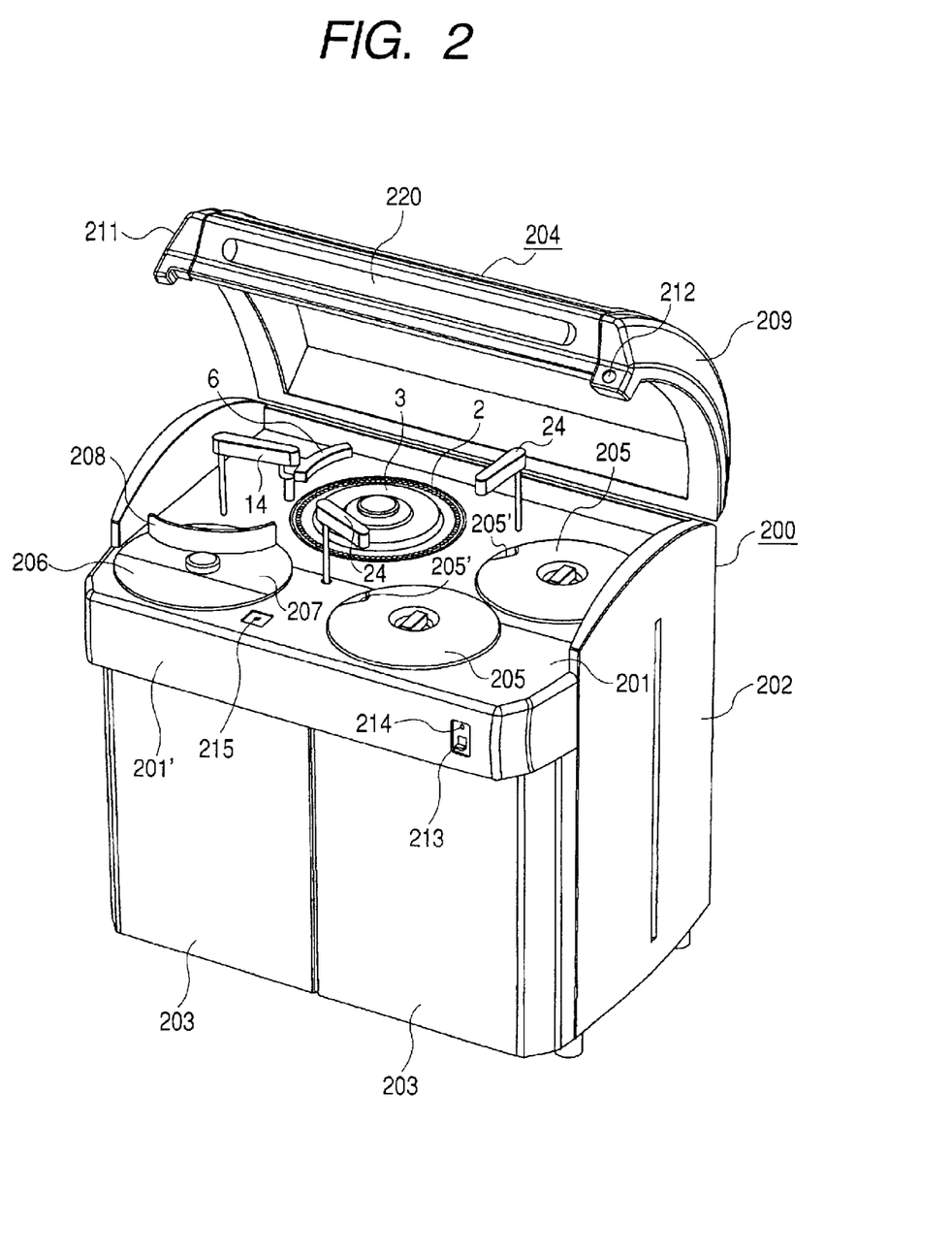
FIG. 2 is a perspective view for showing an outer appearance of a state in which a cover of an automatic analyzer of one preferred embodiment of the present invention is opened.
Figure 3A:
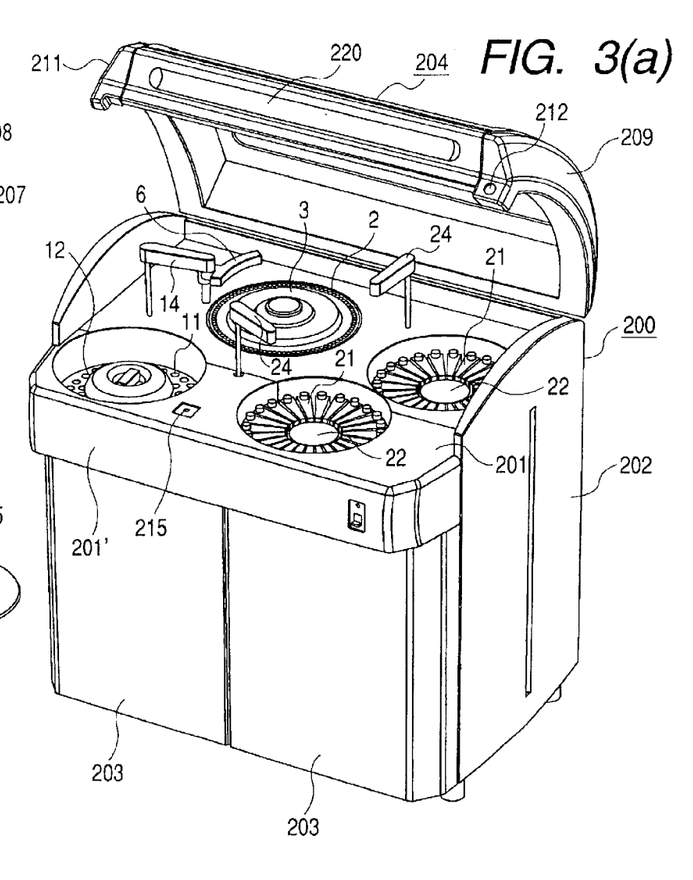
FIG. 3 is a perspective view for showing an outer appearance of a state in which a cover of the automatic analyzer of one preferred embodiment of the present invention and a cover of an internal device are opened and a shape of the cover of the internal device.
Figure 3B:
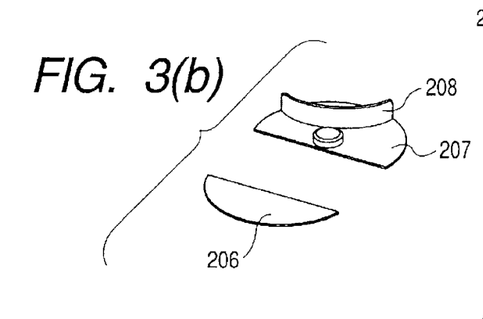
Figure 3C:
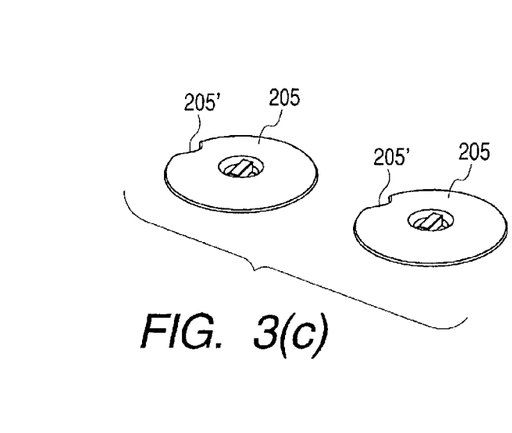
Figure 4:
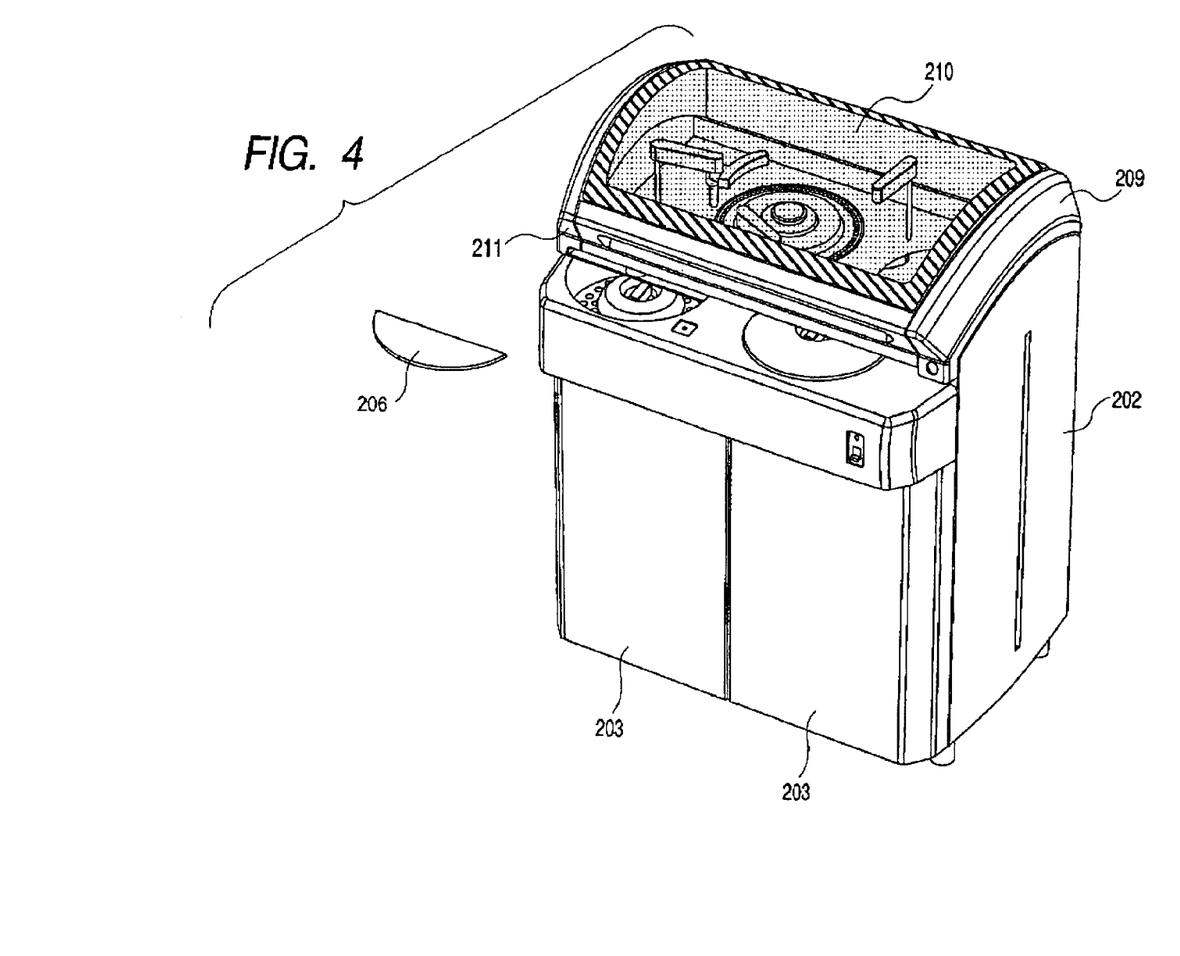
FIG. 4 is a perspective view for showing a state in which a cover of the automatic analyzer of one preferred embodiment of the present invention is closed and only a cover above a reaction disk is removed.
Figure 5A:
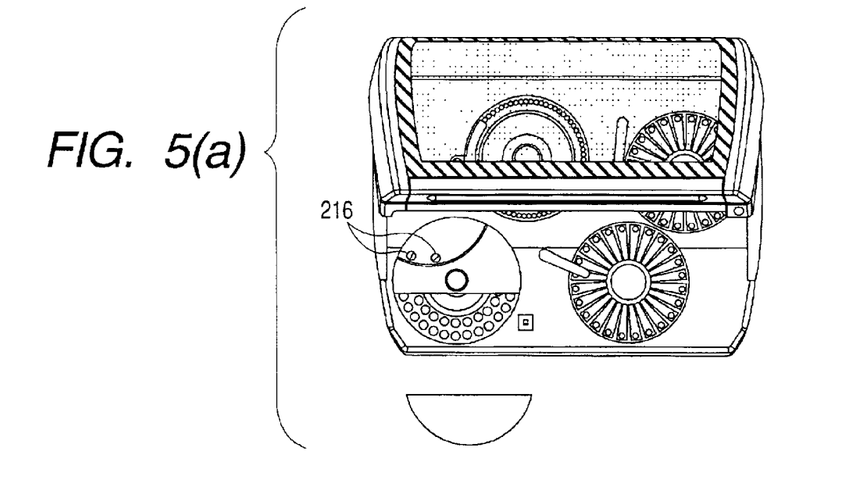
FIG. 5 is a top view for illustrating a size where the reaction disk is exposed outside the cover.
Figure 5B:
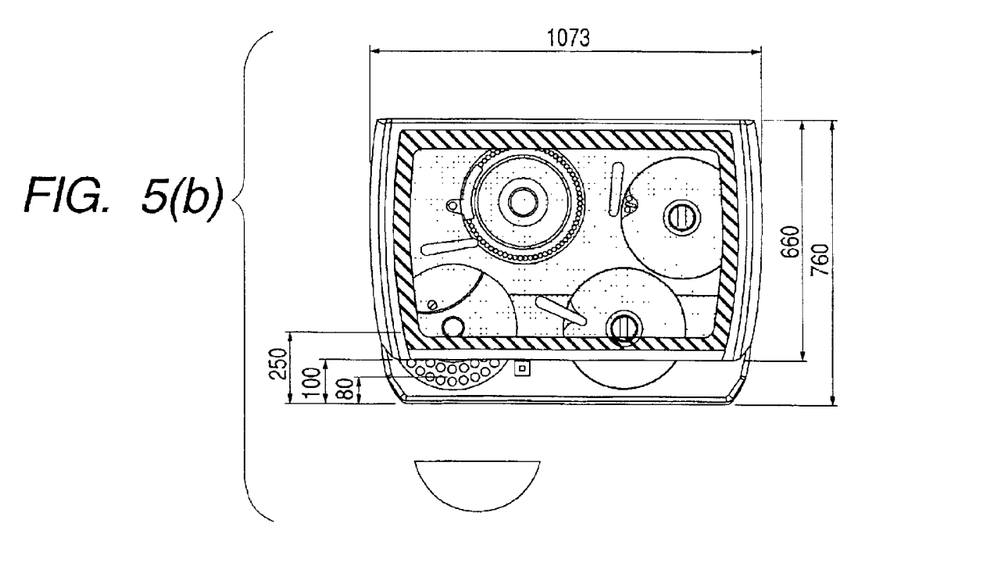
Figure 6:
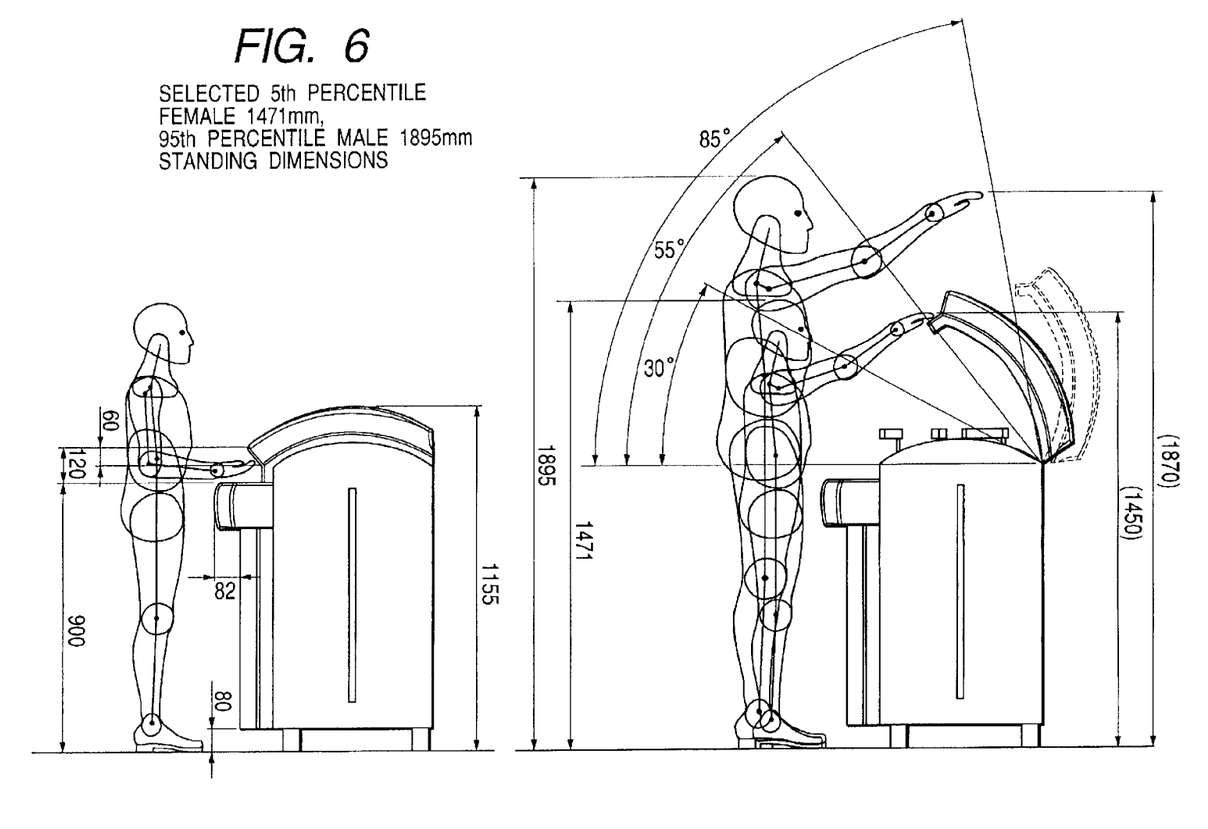
FIG. 6 is a side elevational view for illustrating a size of each of the component elements of the automatic analyzer of one preferred embodiment of the present invention.

FIG. 2 is a perspective view for showing an outer appearance of a state in which a cover of an automatic analyzer of one preferred embodiment of the present invention is opened, FIG. 3 is a perspective view for showing an outer appearance of a state in which a cover of the automatic analyzer of one preferred embodiment of the present invention and a lid of an internal device are opened and a shape of the cover of the internal device, FIG. 4 is a perspective view for showing a state in which a cover of the automatic analyzer of one preferred embodiment of the present invention is closed and only a cover above a reaction disk is removed, FIG. 5 is a top view for illustrating a size where the reaction disk is exposed outside the cover, and FIG. 6 is a side elevational view for illustrating various kinds of size, and then the automatic analyzer of the preferred embodiment of the present invention will be described in reference to these figures. In FIGS. 2 to 6, reference numeral 200 denotes a body; 201 is a top panel; 201' is a front panel; 202 is a side panel; 203 is a front door; 204 is a cover; 205 is a reagent disk cover; 205' is a recess; 206, 207 are sample disk covers; 208 is a protection plate; 209 is a frame; 210 is a transparency board; 211 is eaves; 212 is a keyhole; 213 is a power switch; 214, 215 are an indicator; 216 is a hole; and 220 is a groove.

Each equipment described in reference to FIG. 1 is constructed such that a part of it is stored in the body 200 and the other part of it is arranged to be exposed on the top panel 201 of the body 200. As shown in FIGS. 2 and 3(a), the body 200 is comprised of the top panel 201; the side panel 202 projected out of the top panel 201 and having an upper surface formed like an arcuate shape; two front doors 203; and a rear surface plate (not shown), wherein the cover 204 is arranged to cover a part of the top panel 201. Then, the top panel 201 is provided with a front panel 201' formed to be projected forwardly from the front door 202. The upper surface of the top panel 201 of the body 200 is provided with the sample disk 12 at the left side of the operator (hereinafter called as an operator's side), the reaction disk 3 at the deeper side (hereinafter called as a rear side) of the operator of the sample disk 12, and two reagent disks 22 at the operator's right side and its deeper side. In addition, the upper surface of the top panel 201 of the body 200 is provided with a sample feeder 14 for sucking each of sample liquid from the sample cup 11 of the sample disk 12 into the nozzle 13 held at the movable arm for sample and discharging the sample to the reaction cuvettes 2 at a specified position of the reaction disk 3; the reagent feeder 24; and the rinse mechanism 6 for rinsing the reaction cuvettes 2. Although the mixing mechanism 4 for the reaction liquid and the photometer 5 described in reference to FIG. 1 are also arranged at the upper surface of the top panel 201 of the body 200, their arrangement is not illustrated to avoid any troublesome illustration in the drawings because their arrangement does not constitute the gist of the present invention. In addition, similarly, the nozzles fixed to the feeders 14, 24 are also not illustrated.

The sample disk 12 stores many sample cups 11 arranged in two rows at a periphery of the sample disk 12, wherein sample disk covers 206, 207 removable and divided into two units are arranged to cover the sample disk 12. As described later, the sample disk cover 206 covers the part of the sample disk 12 exposed outside the cover 204 in such a way that it can be removed from outside even in the case that the cover 204 is closed, and the sample disk cover 207 covers the part of the sample disk 12 becoming inside part of it when the cover 204 is kept closed. As shown in FIG. 3(b), the sample disk cover 207 is provided with the protection plate 208. This protection plate 208 is arranged to prevent an operator from accidentally touching the nozzle 13 when the sample liquid is sucked from the sample cup 11 of the sample disk 12 into the nozzle 13 held at the movable arm for sample. The nozzle 13 is of a needle-like member and the sample liquid is frequently blood and the like and there occurs a possibility of infection when the operator touches it. However, arrangement of the aforesaid protection plate 208 enables such an accident as above to be prevented. As shown in FIG. 5(a), two holes 216 becoming a passage for the nozzle 13 held at the movable arm for sample sucking the sample liquid from the sample cup 11 are arranged inside the protection plate 208 of the sample disk cover 207 in correspondence with the row positions of many sample cups 11 arranged in two rows.

The reagent bottles 21 having reagent taking-out ports along the circumferential edge of the disk 22 are stored in each of the reagent disks 22, and there is provided the reagent disk cover 205 removable to cover the reagent disks 22. As shown in FIG. 3(c), the reagent disk cover 205 is provided with a recess 205'. This recess 205' forms a passage where the reagent nozzle 23 arranged at the reagent feeder 24 is inserted into the reagent bottle 21. In addition, the reagent bottle 21 is formed into such a fan shape as one in which its sectional shape is thin, and in the case that many reagent bottles 21 are arranged at the reagent disk 22, the location near the center of the disk can be applied as a bottle portion and the taking-out ports are arranged at the outer circumference of the disk.

Before the location on the top panel 201 of the body 200 and near the sample disk 12 is arranged the indicator 215 of LED or the like lit when the sample disk 12 is not rotated, and further the right side of the front plate 201' are arranged the power switch 213 and a power indicator 214 made of LED or the like. Function of an indicator 215 or the like will be described later.

As apparent from FIGS. 2 to 4, the cover 204 is comprised of a frame 209 and a transparency board 210 and it is attached to the rear side of the top panel 201 of the body 200 by a hinge in such a way that its front surface side is opened upward. The lower surface of the frame 209 placed on the upper part of the side panel 202 is formed into an arcuate shape in compliance with the shape of the upper part of the side panel 202 formed into the arcuate shape, and its upper surface is also formed into an arcuate shape. Accordingly, the transparency board 210 covering the upper surface of the frame 209 is formed with a curved surface with a part of cylinder curled along a curved line formed into an arcuate shape at the side of the frame 209. As apparent from FIG. 4, since the upper surface of the cover 204 is constituted by the transparency board 210, the operator can supervise it easily from outside the situation of the device installed on the top panel 201 of the body 200 under a state in which the cover 204 is closed. Further, in FIG. 4, the portion in the transparency board 210 with a hatched line at its peripheral part is a design pattern for indicating the cover and it may also be applicable that this portion can be eliminated.

As shown in FIG. 4, the front side of the cover 204 forms an eaves 211 by the portion inclined downwardly to cause the upper part to be projected toward the operator's side and the portion abutted at a right angle to the top panel 201 when the cover 204 is closed, wherein the eaves 211 is provided with the groove (recess) 220 to which a hand is engaged when the cover 204 is opened or closed and the lower right side of the eaves 211 is provided with a keyhole 212. The cover 204 is closed for preventing dangerous condition during operation of the automatic analyzer, a key is engaged with the cover 204, and the cover 204 is prevented from being accidentally opened. The aforesaid keyhole 212 is used for applying a key or releasing the key.

In addition, the cover 204 is constituted such that when the cover 204 is closed, it does not cover all the top panel 201 of the body 200 and a part of it at the operator's side is exposed outside the cover 204. A portion exposed outside it is a part of the sample disk cover 206 described above. As described above, the sample disk cover 206 covering the part of the sample disk 12 exposed outside the cover 204 is removed by an operator in the case that the sample cup 11 having the sample required urgently to perform an inspection is set under a state in which the cover 204 is being closed during the operation of the automatic analyzer in such a way that it may be taken out from outside even if the cover 204 is being closed.

Further, during the operation of the analyzer, the feeder for feeding either the sample or the reagent is being operated, and when the cover 204 is opened during the operation of the analyzer to cause the feeder to be exposed and it sometimes occurs that the operator may touch accidentally the feeding needle fixed to the feeder. The preferred embodiment of the present invention is constituted such that the cover 204 can be applied with a lock and the sample cup 11 can be fed to the sample disk 12 even under the state in which the cover 204 is closed and applied with a lock, the portion not required for feeding the sample is not exposed so long as another person other than the person who fed the sample being processed at present does not release the applied lock for the cover 204 in the case that the sample requiring an urgent inspection is generated and in the case that the sample is fed in an interrupted mode into the device being operated to perform an inspection or the like.

Due to this fact, the preferred embodiment of the present invention can prevent a person not familiar with the feeding of the urgent sample or a person other than the operator fed the sample being operated at present from accidentally touching the feeder.

At this time, if the sample disk 12 is being rotated, this state is dangerous, the operator instructs an order to set the sample cup 11 to the sample disk 12 to the computer 50 for controlling operation of each of the mechanisms and processing data through the LCD 52 with touch panel for the input/output operation and displaying operation. With such an arrangement as above, the computer 50 may control the sample disk 12 or the like and stop its rotation, although the indicator 215 described above illuminates green, for example, when the sample disk 12 is completely stopped. The operator acknowledges the illumination of the indicator 215 and removes the sample disk cover 206 covering the part of the sample disk 12. With such an arrangement as above, the operator can set safely the sample cup 11 to the sample disk 12.

As the indicator 215, an indicator illuminated green when the sample disk 12 is stopped and illuminated red during rotation may also be applicable. In addition, when the operator tries to remove the sample disk cover 206 during rotation of the sample disk 12, it is possible to generate an alarm sound alarming that the sample disk 12 is being rotated.

Although the cover 204 is being closed when the sample cup 11 is set on the sample disk 12, as described above, the front surface of the cover 204 is formed with the eaves 211 by the portion inclined at its upper part to be projected toward the operator's side and by the portion abutted against the top panel 201 at a right angle, so that the operator can set the sample cup 11 to the sample disk 12 while the front surface of the cover 204 does not become a hindrance.

In FIGS. 5(*a*), (*b*) is shown a top plane view for showing each of the state in which the cover 204 is opened and the state in which the cover 204 is closed, respectively. As shown in FIG. 5(*a*), as already described, inside the protection plate 208 for the sample disk cover 206 are arranged two holes 216 acting as passages for the nozzle 13 held at the movable arm for the sample to suck sample liquid through the sample cup 11 in correspondence with the row positions of many sample cups 11 arranged in two rows. As shown in FIG. 5(*b*), a size of the automatic analyzer of the preferred embodiment of the present invention is 1,073 mm in a width and 760 mm in a depth. Then, the depth size of the cover 204 is illustrated as 660 mm in the illustrated example. The depth size of the cover 204 is a size where the operator's side of the top panel 201 of the body 200 is exposed when the cover 204 is closed, the width of the exposed segment is satisfactory to such a size as one in which the sample cup 11 can be easily set in the sample disk 12 after removing the sample disk cover 206, this is approximately 100 mm in the case that the sample cups 11 are arranged in two rows around the sample disk 12 and in turn this is approximately 80 mm in the case that the sample cups 11 are arranged in one row around the sample disk 12.

The aforesaid exposing width is not restricted to the aforesaid width, but it is satisfactory to have a size satisfying the condition capable of easily setting the sample cups 11 in the aforesaid sample disk 12, and as shown in FIG. 5(*b*), for example, it is satisfactory that the size ranges from 80 mm to approximately 250 mm as a standard value at the central position of the sample disk.

Then, referring now to FIG. 6, a height size of the automatic analyzer of the preferred embodiment of the present invention will be described as follows. In FIG. 6(*a*), this figure shows a state in which a short adult woman stands in front of the automatic analyzer under the closed state of the cover 204 trying to open the cover 204. When the cover 204 is opened, the woman applies a hand to the eaves 211 of the cover 204 and pulls it upward. As shown in FIG. 6(a), even the short woman can apply the hand to the groove 220 arranged at the eaves 211 of the cover 204 under a state in which the arm is bent at a right angle by setting the height up to the top panel 201 of the device to about 900 mm and can pull up the cover 204 to open it. Further, in FIG. 6(a) are shown the sizes of other portions, although these sizes are not restricted to the indicated values.

In FIG. 6(b) is illustrated a state in which a short adult woman and a tall adult man stand in front of the automatic analyzer with its cover 204 being opened and they are trying to close the cover 204. A main gist under the state in which the cover 204 is opened consists in the fact that the operator can sufficiently look into the deep side of the cover 201 while standing in front of the device and the fact that the operator applies a hand to the groove 220 arranged at the eaves 211 of the opened cover 204 and can easily close the cover 204. As apparent from FIG. 6(b), although the cover 204 is opened by about 30°, the short woman can see sufficiently up to the deep side of the cover 201, the tall man cannot sufficiently see up to the deep side of the cover 201. Then, when the cover 204 is opened by about 55°, both short woman and tall man can see sufficiently up to the deep location of the top panel 201.

At this time, even the short woman can apply a hand to the groove 220 arranged at the eaves 211 of the opened cover 204 to easily close the cover 204 while standing upright in front of the device. Further, as the cover 204 is opened up to about 85°, in the case of short woman, the woman can extend the hand and apply the hand to the lower end of the eaves 211 of the opened cover 204.

Accordingly, in order for the short woman to easily perform Aid to open or close the cover 204, the angle to open the cover 204 is the most preferable opening or closing angle from about 30° to about 55° and in the case of tall man, its most preferable angle is from about 55° to about 85°. When the cover 204 is opened by about 55°, in the case of the tall man, either the sample disk or the reagent disk arranged at the upper surface of the device is hidden from his line of sight by the cover 204, although the cover 204 is formed with the transparency board 210, so that the sample disk or the like can be visually acknowledged through the transparency board 210. However, in order to perform a maintenance or an inspection of equipment installed on the top panel 201 of the device, opening of the cover 204 up to 90° facilitates its operation.

In the foregoing arrangement, there is provided a mechanism capable of fixing the opening angle of the cover 204 at an optional angle when the cover 204 is opened by more than 30° if the cover 204 is opened, the operator can open the cover 204 at such a position where the most suitable angle for a height of either a woman or a man is applied when the cover 204 is opened under a state of use of normal case.

As described above, in accordance with the present invention, it is possible to provide a small-sized automatic analyzer convenient in use in which the urgent sample can be easily inserted, its safety in operation as well as an operability of the operator can be improved and its erroneous operation can be prevented.

What is claimed is:

1. An automatic analyzer for performing a biochemical inspection or an immunity inspection, comprising:
    a body having a top panel;
    a sample disk provided in the top panel for storing a plurality of sample cups;
    a reagent disk provided in the top panel for storing a plurality of reagent bottles;
    a reaction disk provided in the top panel for storing a plurality of reaction cuvettes for reacting sample liquid in said sample cups with reagent in the reagent bottles;
    a sample feeder provided in the top panel for sucking a predetermined amount of sample liquid from a sample cup in a specified position of said sample disk in response to sample information and for discharging the sample liquid to a reaction cuvette at a specified position of said reaction disk;
    a cover movable between an open position and a closed position, the closed position covering the sample feeder, the reaction disk and a part of the sample disk; and
    a sample disk cover for covering the sample disk, the sample disk cover comprising two units, one of the two units being removable and being exposed outside the cover when the cover is in the closed position.

2. The automatic analyzer according to claim 1, further comprising a reagent feeder for sucking a predetermined amount of reagent liquid from a reagent bottle in a specified position of said reagent disk in response to information from the reagent bottle at the specified position of said sample disk and for discharging the reagent liquid to a reaction cuvette at a specified position of said reaction disk reagent, wherein the reagent feeder provided in the top panel at a position that is covered with the cover when the cover is in the closed position.

3. The automatic analyzer according to claim 1, wherein another of the two units of the sample disk cover is provided with a protection plate for protecting an operator from accidentally touching a nozzle of the sample feeder.

4. The automatic analyzer according to claim 1, wherein the cover has an upper curved surface, a lower portion abutted against the top panel at a right angle when the cover is in the closed position, and an eaves portion formed by a portion of the upper curved surface projecting downwardly and beyond the lower portion towards an operators side of the automatic analyzer, wherein at least part of the upper curved surface of the cover is transparent.

5. The automatic analyzer according to claim 1, wherein the sample feeder comprises a nozzle carried on a movable arm and a pipettor connected to the nozzle.

6. The automatic analyzer according to claim 5, wherein another of the two units of the sample disk cover is provided with a protection plate for protecting an operator from accidentally touching a nozzle of the sample feeder.

7. The automatic analyzer according to claim 6, wherein the another of the two units of the sample disk cover is provided with at least one passage through which the nozzle of the sample feeder can pass, the at least one passage being provided on a side of the protection plate away from an operators side of the automatic analyzer.

8. The automatic analyzer according to claim 1, wherein the cover is provided with a lock for locking the cover in the closed position.

9. The automatic analyzer according to claim 2, wherein the reagent feeder comprises a nozzle carried on a movable arm and a pipettor connected to the nozzle.

10. The automatic analyzer according to claim 9, further comprising a reagent disk cover for covering the reagent disk.

11. The automatic analyzer according to claim 10, wherein the reagent disk cover is provided with a passage through which a nozzle of the reagent feeder can pass.

* * * * *